United States Patent
Choi et al.

(10) Patent No.: US 12,011,491 B2
(45) Date of Patent: Jun. 18, 2024

(54) SHEET TYPE MASK GEL COMPOSITION, MASK SHEET COMPRISING THE SAME, AND MANUFACTURING METHOD OF MASK SHEET

(71) Applicant: AMOREPACIFIC CORPORATION, Seoul (KR)

(72) Inventors: Yanggyu Choi, Yongin-si (KR); Jiwook Jang, Yongin-si (KR); Myoungwoo Kim, Yongin-si (KR); Jaemin Lim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 417 days.

(21) Appl. No.: 17/213,350

(22) Filed: Mar. 26, 2021

(65) Prior Publication Data
US 2021/0299003 A1    Sep. 30, 2021

(30) Foreign Application Priority Data
Mar. 27, 2020   (KR) .......................... 10-2020-0037590

(51) Int. Cl.
*A61K 8/02*      (2006.01)
*A45D 44/00*     (2006.01)
(Continued)

(52) U.S. Cl.
CPC .......... *A61K 8/0212* (2013.01); *A45D 44/002* (2013.01); *A61K 8/345* (2013.01); *A61K 8/73* (2013.01); *A61K 8/735* (2013.01); *A61K 8/8111* (2013.01); *A61K 8/85* (2013.01); *A61M 35/10* (2019.05); *A61M 2207/00* (2013.01)

(58) Field of Classification Search
CPC ........ A61K 8/0212; A61K 8/345; A61K 8/73; A61K 8/735; A61K 8/8111; A61K 8/85; A61K 2800/884; A61K 8/042; A61K 8/731; A61K 8/732; A61K 8/736; A61K 8/8152; A61K 8/86; A61K 8/06; A61K 2800/48;
(Continued)

(56) References Cited

U.S. PATENT DOCUMENTS 5,980,925 A    11/1999   Jampani et al.
6,432,428 B1   8/2002    Arquette et al.
(Continued)

FOREIGN PATENT DOCUMENTS

CN    105476867 A    4/2016
CN    111419773 A    7/2020
(Continued)

OTHER PUBLICATIONS

Lipoid, Soybean Phospholipids & Formulations, https://lipoid.com/en/products/raw-material-sources/soybean-phospholipids-formulations/; accessed Dec. 16, 2022 (Year: 2022).
(Continued)

*Primary Examiner* — Frederick F Krass
*Assistant Examiner* — Lucy M Tien
(74) *Attorney, Agent, or Firm* — Sughrue Mion, PLLC

(57) ABSTRACT

One aspect of the present disclosure is a sheet type mask gel composition including a polyol, a water-soluble thickener, and water, wherein adhesive strength is maintained for a long time, a mask sheet including the same, and a method of manufacturing the mask sheet.

18 Claims, 3 Drawing Sheets

(51) Int. Cl.
  *A61K 8/34* (2006.01)
  *A61K 8/73* (2006.01)
  *A61K 8/81* (2006.01)
  *A61K 8/85* (2006.01)
  *A61M 35/00* (2006.01)

(58) Field of Classification Search
  CPC . A45D 44/002; A61M 35/10; A61M 2207/00; A61Q 19/00; A61Q 19/08
  USPC ........................................................ 604/294
  See application file for complete search history.

(56) References Cited

U.S. PATENT DOCUMENTS

| | | | |
|---|---|---|---|
| 2006/0104931 A1* | 5/2006 | Fukutome | A61K 8/733 424/70.13 |
| 2016/0015619 A1 | 1/2016 | Lee | |
| 2019/0345336 A1 | 11/2019 | Addy et al. | |

FOREIGN PATENT DOCUMENTS

| | | |
|---|---|---|
| JP | 2000-226325 A | 8/2000 |
| JP | 2005-97124 A | 4/2005 |
| KR | 10-2012-0054906 A | 5/2012 |
| KR | 10-1497040 B1 | 3/2015 |
| KR | 10-1497653 B1 | 3/2015 |
| KR | 10-2015-0125669 A | 11/2015 |
| KR | 10-2016-0081382 A | 7/2016 |
| KR | 10-1770556 B1 | 8/2017 |
| KR | 10-2018-0027858 A | 3/2018 |
| KR | 10-2018-0050335 A | 5/2018 |
| WO | 2008/040303 A1 | 4/2008 |

OTHER PUBLICATIONS

Sigma Aldrich, L-a-Phosphatidylcholine, hydrogenated, https://www.sigmaaldrich.com/US/en/product/sigma/p4139; accessed Dec. 20, 2022 (Year: 2022).

Oliphantetal., Effect of Jojoba Esters on Skin Barrier Function, Skin Hydration, and Consumer Preference, https://www.floratech.com/PDFs/Articles_MKT/ART06.pdf; accessed Dec. 20, 2022; published 2013 (Year: 2013).

Wikipedia, Jojoba ester, https://en.wikipedia.org/wiki/Jojoba_ester; accessed Dec. 16, 2022 (Year: 2022).

Fifty Shades of Snail, Reader Questions: Why I Use Sheet Masks After Serums, https://fiftyshadesofsnail.com/2016/12/05/reader-questions-why-i-use-sheet-masks-after-serums/; accessed Dec. 23, 2022; archived via Wayback Machine Dec. 21, 2016 (Year: 2016).

Dermovia, Lace Your Face Calming Chamomile, https://www.dermovia.com/products/calming-chamomile-face-mask; accessed Dec. 23, 2022 (Year: 2022).

Dermaviduals, Nanoparticles in cosmetic products - good or bad?, https://dermaviduals.de/english/publications/special-actives/nanoparticles-in-cosmetic-products-good-or-bad.html; accessed Dec. 20, 2022; archived via Wayback Machine Sep. 21, 2010 (Year: 2010).

Cornier et al., Nanocosmetics: From Ideas to Products, 2019, Springer Nature Switzerland, 1,97-140 (Year: 2019).

* cited by examiner

SHEET TYPE MASK GEL COMPOSITION, MASK SHEET COMPRISING THE SAME, AND MANUFACTURING METHOD OF MASK SHEET

CROSS-REFERENCE TO RELATED APPLICATION

This application claims priority to and the benefit of Korean Patent Application No. 10-2020-0037590 filed in the Korean Intellectual Property Office on Mar. 27, 2020, the entire contents of which are incorporated herein by reference.

BACKGROUND OF THE INVENTION

(A) Field of the Invention

This disclosure relates to a sheet type of mask gel composition, a mask sheet including the same, and a manufacturing method of the mask sheet.

(b) DESCRIPTION OF THE RELATED ART

Human skin plays a fundamental role in protecting various parts of a body from external stimuli, and also conducts important functions of making a person stand out by expressing clean and bright skin or clear and soft skin through skin care or making the skin healthy.

In such skin care, particularly, since an exposed area such as a face, a neck, or the like is a channel for active personal expression to the outside, the demand for skin care products such as mask sheets is rapidly increasing.

Such a cosmetic mask sheet is manufactured by adding a face lotion or functional ingredients to a base sheet to impart efficacy of relieving tension of the skin, moisturizing the skin, improving elasticity, relieving wrinkles, removing waste and adsorbed contaminants on the skin surface, eliminating excessive sebum, promoting slipperiness, providing psychological stability, supplying nutrients, and the like.

Since this is in line with a human desire of keeping clean and healthy skin, the mask sheet market is gradually growing, and in addition, as concerns about skin damage due to environmental pollutants draw attention, the market size is more rapidly growing in recent years.

Above all, in recent years, in order to improve moisture retention, a hydrogel mask sheet having a three-dimensional hydrophilic polymer network has been gaining popularity.

However, the hydrogel mask sheet is water-phased and thus is not suitable for delivering oil-soluble active ingredients, and in addition, it includes a large amount of moisture and thus is vulnerable to microbial contamination, and above all, is not easily adhered to the skin due to low gel adhesion and thus insufficiently delivers the active ingredients to the skin.

In particular, with the recent development of layering skin care or layered make-up, a cosmetic method of first applying a water-soluble/oil-soluble composition such as a cream or an essence to bare skin and then attaching the mask sheet instead of simply attaching the mask sheet to the bare skin is becoming more and more popular, but since all conventional mask sheets exhibit significantly-decreased adhesion to the skin on which the cream or essence is applied, almost all of the mask sheets currently available on the market may not be suitable for the layering skin care.

Furthermore, if the mask sheets are attached to the skin immediately after being opened, there is no problem, but if the mask sheets are attached to the skin after a certain period of time, there may be a problem of not delivering the active ingredients contained therein to the skin because of evaporation of moisture in the mask sheets. Most of the mask sheets currently available on the market quickly dry out when left at room temperature even for a little while and thus may not fully function as a mask sheet.

Therefore, development of a mask sheet having a new composition capable of solving such problems is required.

SUMMARY OF THE INVENTION

An embodiment is to provide a sheet type of mask gel composition having superior adhesion to that of a conventional mask sheet, and particularly, being optimized for layering skin care, a mask sheet including the same, and a method of manufacturing the mask sheet.

According to an embodiment, a sheet type of mask gel composition includes a polyol, a water-soluble thickener, and water, wherein adhesive strength is maintained after being adhered and used for a long time, for example greater than or equal to about 30 minutes, greater than or equal to about 1 hour, greater than or equal to about 2 hours, greater than or equal to about 3 hours, greater than or equal to about 4 hours, greater than or equal to about 5 hours, greater than or equal to about 6 hours, greater than or equal to about 7 hours, greater than or equal to about 8 hours, greater than or equal to about 9 hours, greater than or equal to about 10 hours, greater than or equal to about 11 hours, greater than or equal to about 12 hours, or about 12 hours to about 24 hours.

The sheet type of mask gel composition may satisfy Equation 1.

$$100-(B/A\times100)<10 \quad\quad \text{[Equation 1]}$$

Herein, A is a weight immediately after the gel obtained by gelling the gel composition is optionally processed to a size of 5 cm×5 cm×1 mm, and B is a weight immediately after drying the gel immediately after arbitrary processing at 45° C. for 60 minutes.

The sheet type of mask gel composition may have higher adhesive strength when the sheet type of mask gel composition is applied to the skin of a mammal, after applying the water-soluble or oil-soluble composition to the skin of a mammal than when the sheet type of mask gel composition alone is applied directly to the skin of a mammal.

The sheet type of mask gel composition may further include a wrinkle-improving material, a whitening material, a skin trouble-improving material, or a combination thereof.

The sheet type of mask gel composition may have adhesive strength of greater than or equal to about 0.6 N/cm².

The polyol may be included in an amount of about 60 wt % to about 98 wt % based on a total amount of the sheet type of mask gel composition.

The polyol may include glycerine, 1,3-butanediol, propylene glycol, polyethylene glycol, dipropylene glycol, propanediol, or a combination thereof.

The water-soluble thickener may be included in an amount of about 0.01 wt % to about 20 wt % based on a total amount of the sheet type of mask gel composition. The water-soluble thickener may include xanthan gum, hyaluronic acid, carboxymethyl cellulose, polyacrylate carboxymethyl starch, carboxymethyl chitosan, carboxymethyl dextran, or a combination thereof.

The sheet type of mask gel composition may be a composition for care of wrinkles, such as a composition for care of neck wrinkles or a composition for care of wrinkles around the eyes or nasolabial areas, and therefore may be a gel composition for a neck mask (neck band), a gel composition for an eye mask, or a gel composition for a facial mask.

According to another embodiment, a mask sheet including the sheet type of mask gel composition is provided.

The mask sheet may be a neck band, a neck mask, an eye mask, or a facial mask.

The mask sheet may have a support attached to one surface of the mask sheet.

The support may be a regenerated fiber such as cotton, rayon, etc., an ester-based material including elastic polyurethane, acetate, wool, polyethylene glycol terephthalate, etc., a nonwoven fabric or a woven fabric made of a fiber of polyethylene, nylon, polypropylene, or a combination thereof, oriented polypropylene, cast polypropylene, high density polyethylene, low density polyethylene, linear low density polyethylene, or a support in which the material is laminated to a nonwoven fabric in the form of a film.

The mask sheet may have a release film attached to the other surface of the mask sheet to which the support may be attached.

Any release film may be used as long as it is a release film or a laminate thereof that is commonly used in transdermal formulations such as a mask pack. For example, the release film may be a film such as polypropylene, polyethylene, polyester, polyvinyl chloride, polyvinylidene chloride, or paper on which the above-mentioned materials are laminated.

According to an embodiment, a method of manufacturing a mask sheet includes: uniformly applying the stirred mixture of a polyol, a water-soluble thickener, and water to a release film; uniformly applying the contents to a release film and then heating and cooling to perform gelation; and attaching a support to the surface of the contents on which the release film is not applied to manufacture a mask sheet, wherein the mask sheet maintains its adhesive strength after being adhered to the skin for a long time, for example greater than or equal to about 30 minutes, greater than or equal to about 1 hour, greater than or equal to about 2 hours, greater than or equal to about 3 hours, greater than or equal to about 4 hours, greater than or equal to about 5 hours, greater than or equal to about 6 hours, greater than or equal to about 7 hours, greater than or equal to about 8 hours, greater than or equal to about 9 hours, greater than or equal to about 10 hours, greater than or equal to about 11 hours, greater than or equal to about 12 hours, or about 12 hours to about 24 hours.

The mask sheet manufacturing method may further include aging the gel attached to the support.

The heating is performed at a temperature of about 70° C. to about 120° C. for about 2 minutes to about 30 minutes.

The stirred mixture of the polyol, water-soluble thickener, and water may further include a wrinkle-improving material, a whitening material, a skin trouble-improving material, or a combination thereof.

One aspect of the present disclosure may provide a sheet type of mask gel composition having excellent adhesion and thus more excellent delivery capability of active ingredients to the skin within a short time, when subsequently used after applying a cream or an essence composed of a water-soluble or oil-soluble composition than when used alone, a mask sheet including the same, and a method of manufacturing the mask sheet.

DETAILED DESCRIPTION OF THE EMBODIMENTS

Figure 1:
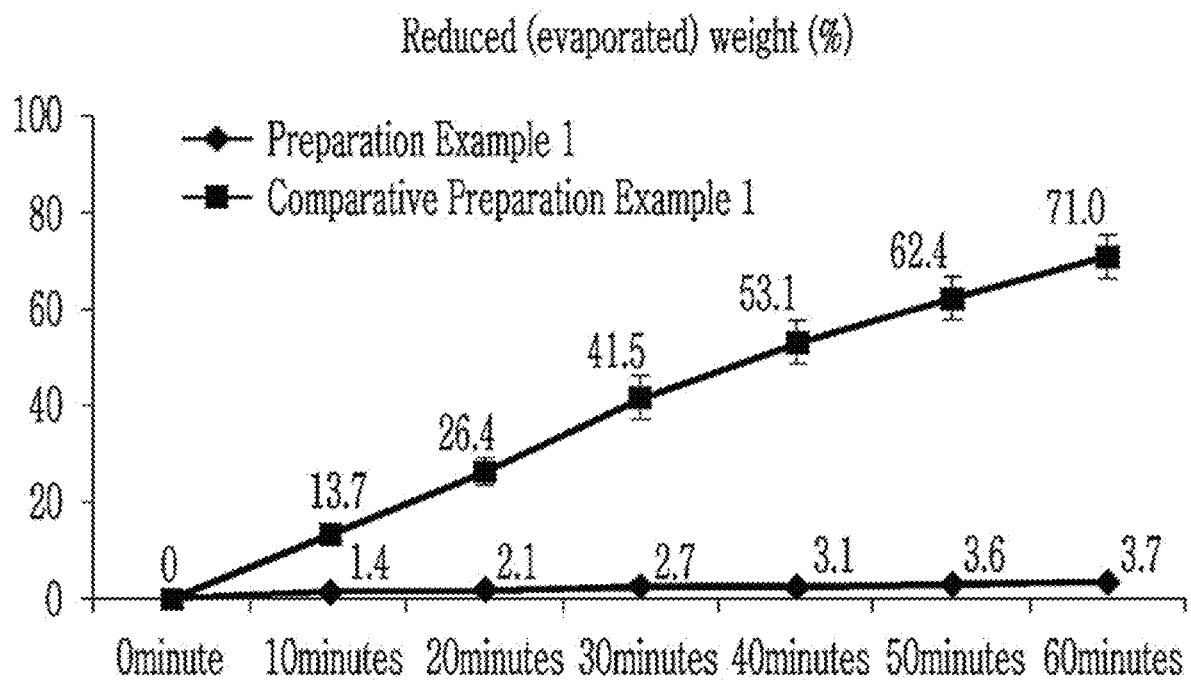
FIG. 1 is a graph showing each loss-on-drying test result of the gel composition specimen of Preparation Example 1 and a hydrogel composition specimen.
Figure 2:
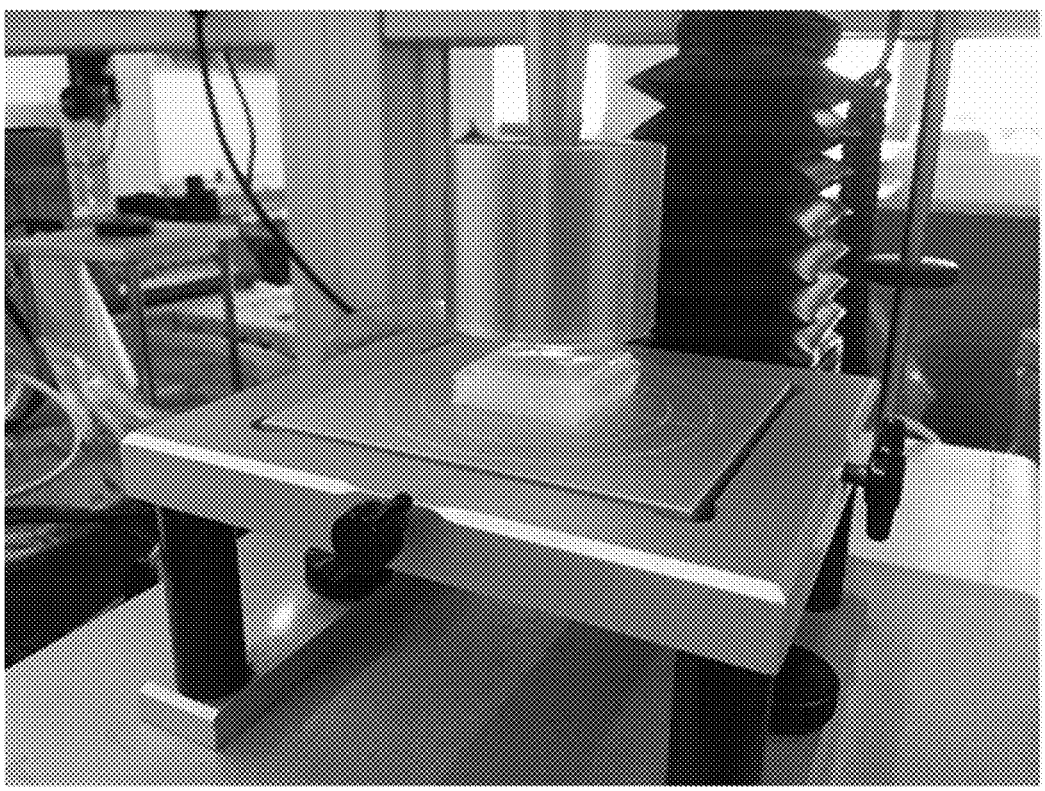
FIGS. 2 and 3 are photographs independently showing that the adhesive strength of a sheet type of mask gel composition or a mask sheet including the same is measured by using a texture analyzer.

Hereinafter, embodiments of one aspect of the present disclosure will be described in detail so that those of ordinary skill in the art can easily implement one aspect of the present disclosure.

However, this disclosure may be embodied in many different forms and is not to be construed as limited to the embodiments set forth herein.

The terms used in the present specification are defined in consideration of functions in one aspect of the present disclosure, and these may vary according to the intention or custom of users or operators, and thus the definitions herein for describing the "mask sheet" according to one aspect of the present disclosure are to be made based on the overall contents.

In the present specification, it will be understood that when an element such as a layer, film, region, or substrate is referred to as being "on" another element, it may be directly on the other element or intervening elements may also be present.

In contrast, when an element is referred to as being "directly on" another element, there are no intervening elements present.

In the present specification, that adhesive strength is maintained means that when a gel composition, a mask sheet, or the like is attached to skin of a mammal such as a human, the gel composition or mask sheet does not fall off from the skin and simultaneously keeps being attached to the skin for a certain period of time from when the gel composition or the mask sheet is attached to the skin, for example greater than or equal to about 30 minutes, greater than or equal to about 1 hour, greater than or equal to about 2 hours, greater than or equal to about 3 hours, greater than or equal to about 4 hours, greater than or equal to about hours, greater than or equal to about 6 hours, greater than or equal to about 7 hours, greater than or equal to about 8 hours, greater than or equal to about 9 hours, greater than or equal to about 10 hours, greater than or equal to about 11 hours, greater than or equal to about 12 hours, or greater than or equal to about 24 hours.

Specifically, in the present specification, that adhesive strength is maintained means that when a gel composition, a mask sheet, or the like is attached to skin of a mammal such as a human (an adhered area of 100%), the gel composition or mask sheet does not fall off from the skin and simultaneously keeps being attached at greater than or equal to about 70% of the skin for greater than or equal to about 30 minutes and specifically, greater than or equal to about 4 hours after attaching the gel composition, the mask sheet, or the like to the skin.

Hereinafter, a sheet type of mask gel composition according to an embodiment is illustrated.

In order to ameliorate the problems of conventional non-woven fabric mask sheets, hydrogel mask sheets have been developed and are now widely being used, but since a hydrogel contains a large amount of moisture and thus has physical properties such that it is vulnerable to microbial contaminations, there are many difficulties in applying the hydrogel to products.

Specifically, the hydrogel mask sheets are manufactured by using a composition in which a hydrophilic polymer is added to water with other raw materials or a composition in which the hydrophilic polymer is added to an aqueous solution including the other raw materials, wherein the composition generally forms a crosslinked structure, but the crosslinked structure has weak durability and thus deteriorates properties of finally manufactured mask sheets and particularly, elongation or tensile strength thereof. In addition, in order to reinforce the durability of the crosslinked structure, extra additives and the like have been added thereto, but the additives have harmful effects on the skin or change viscosity of the composition and thus make it impossible to manufacture the mask sheet itself.

Furthermore, the hydrogel mask sheets contain an excessive amount of water and are always open to microbial contamination, and when left at room temperature, the mask sheets may quickly become dry.

Accordingly, the demand of consumers for a mask sheet which is differentiated from the conventional hydrogel mask sheets is increasing.

In addition, in recent years, layering skin care has drawn attention, and the conventional mask sheets as well as the aforementioned hydrogel mask sheets have unsuitable physical properties for the layering skin care.

The layering skin care refers to a skin treatment of sequentially applying various types of compositions or sheets to skin over time.

Conventionally, a mask sheet is directly applied to bare skin, but recently, according to the layering skin care, the mask sheet is subsequently attached to the skin after applying a composition (cream or essence, etc.) of a water-soluble or oil-soluble component to the skin, so that active ingredients of the mask sheet have synergistic effects with the cream or essence (e.g., improving functionality such as wrinkle treatment and whitening in a faster time).

However, in order to apply the layering skin care, the mask sheet has excellent adhesive strength, even when attached to skin applied with a cream or essence, but all the hydrogel mask sheets known to date have physical properties that deteriorate the adhesive strength when the layering skin care is applied.

In other words, various products (toners, emulsions, creams, etc.) for skin care are currently being widely used, and since new customer experiences and needs for the skin care are continuously increasing, the conventional hydrogel mask sheets containing a large amount of moisture with acrylic acid and the like as a main component are very short of meeting the new customer needs.

In addition, most other mask sheets claiming excellent adhesive strength on the market, which are not the hydrogel mask sheets, are oil gel formulations using a hydrophobic adhesive base or silicon gel types using silicon materials but also exhibit excellent adhesive strength to bare skin, but still have insufficient adhesive strength to skin applied with a toner, an emulsion, a cream, and the like and thus easily fall off, and accordingly, are limited in playing an essential role of a mask sheet that sufficiently delivers active ingredients to the skin.

However, since the sheet type of mask gel composition according to an embodiment is based on a polyol and a water-soluble thickener, the gel composition exhibits such excellent adhesive strength so as to still maintain the adhesive strength, even if allowed to stand at room temperature, for example, at about 15° C. to about 45° C. for about 24 hours and thus easily supports the active ingredients, and in addition, may be used after using conventional leave-on products (toner, essence, cream, etc.) as well as used alone.

In addition, the gel composition does not contain a large amount of water like the hydrogel formulation and thus is not cold when applied to the skin, and is not stuffy but is comfortable like an oil gel formulation, and also, is inexpensively manufactured, and accordingly, may support both hydrophilic active ingredients and hydrophobic active ingredients and contains a large amount of the polyol (e.g., the polyol may be included in an amount of about 60 wt % to about 98 wt %, for example, about 70 wt % to about 95 wt %, based on a total amount of the sheet type of mask gel composition) and thus may be easily manufactured into products without special preservatives.

The sheet type of mask gel composition according to an embodiment contains a large amount of the polyol and a water-soluble thickener, and thus may secure moisturizing and softness and efficiently deliver water-soluble active ingredients.

In addition, a carboxyl group in the water-soluble thickener reacts with a hydroxy group of the polyol, dramatically reducing moisture during the preparation of the gel composition and forming an insoluble gel, and this gel has very high adhesion and thus may be easily attached to the skin and have excellent effects of delivering the active ingredients to the skin.

In particular, the sheet type of mask gel composition according to an embodiment has very excellent adhesive strength.

Specifically, the sheet type of mask gel composition may satisfy Equation 1.

$$100-(B/A\times 100)<10 \qquad [\text{Equation 1}]$$

Herein, A is a weight immediately after the gel obtained by gelling the gel composition is optionally processed to a size of 5 cm×5 cm×1 mm, and B is a weight immediately after drying the gel immediately after the arbitrary processing at 45° C. for 60 minutes.

In order to maintain the adhesive strength of the gel composition and a mask sheet including the same for a long time, it is important to maintain its initial composition while attached, and the conventional hydrogel or general mask sheets are not suitable for long-term use because moisture is volatilized from a finished hydrogel or a mask sheet itself and thereby adhesive strength is deteriorated so it is not particularly suitable for a subsequent use after using the existing leave-on products.

However, the sheet type of mask gel composition according to an embodiment exhibits almost no composition change but well maintains adhesive strength while attached, which may be confirmed by unpacking the gel composition or mask sheet, removing a release film therefrom, and comparing an initial weight right after exposure to the outside and a weight after a certain period of time to obtain a dried amount and thus check whether or not the initial adhesive strength is maintained.

Specifically, when Equation 1 is satisfied, since the initial adhesive strength is well maintained, even if attached for a long time, for example greater than or equal to about 30 minutes, greater than or equal to about 1 hour, greater than or equal to about 2 hours, greater than or equal to about 3 hours, greater than or equal to about 4 hours, greater than or equal to about 5 hours, greater than or equal to about 6 hours, greater than or equal to about 7 hours, greater than or equal to about 8 hours, greater than or equal to about 9 hours, greater than or equal to about 10 hours, greater than or equal to about 11 hours, greater than or equal to about 12 hours, or about 24 hours, the gel composition or the mask sheet maintains almost the same level of adhesive strength as before attached.

In addition, the gel composition or the mask sheet satisfying Equation 1 may have at least about 80% of the initial adhesive strength (100%) or higher when the sheet type of mask gel composition or the mask sheet is applied or attached after applying water-soluble or oil-soluble compositions (the existing leave-on products and the like) to skin of a mammal than when the sheet type of mask gel composition or the mask sheet alone is directly applied or attached to the skin of a mammal.

As aforementioned, when the gel composition or the mask sheet is used after using the existing leave-on products and the like, the gel composition or the mask sheet may exhibit more excellent adhesive strength, because the gel composition or the mask sheet does exhibits almost no composition change over time.

In other words, other conventional mask sheets exhibit deteriorated adhesive strength, when different compositions are applied in attached areas by using the leave-on products and the like, but the gel composition or the mask sheet according to an embodiment exhibits more excellent adhesive strength when subsequently used after using the conventional leave-on products and the like than when used alone.

The conventional hydrogel or general mask sheets exhibit adhesive strength differences with rapid weight losses, when unpacked for use (attached to the skin) and exposed to the outside, and in addition, since moisture in the leave-on products and the like is added thereto and thus inhibits the adhesive strength, when the conventional hydrogel or general masks are subsequently attached after using the existing leave-on products and the like the adhesive strength itself is more greatly deteriorated than when used alone, and accordingly, the conventional hydrogel or general mask sheets may not be suitable for the layering skin care in which mask sheets and the like are attached after applying cosmetic compositions (cosmetics).

For example, the sheet type of mask gel composition or the mask sheet including the same according to an embodiment may have adhesive strength of greater than or equal to about 0.6 N/cm$^2$, for example, about 0.6 N/cm$^2$ to about 1.5 N/cm$^2$, or about 0.9 N/cm$^2$ to about 1.5 N/cm$^2$.

The adhesive strength is based on the use of the sheet type of mask gel composition or the mask sheet including the same alone, and when the sheet type of mask gel composition or the mask sheet including the same is used after using the leave-on products such as creams and the like, the adhesive strength may be further increased.

For example, when the layering skin care is applied, the adhesive strength may be about 0.4 N/cm$^2$ to about 0.6 N/cm$^2$ higher than the adhesive strength when used alone.

The adhesive strength of greater than or equal to about 0.6 N/cm$^2$ is higher than the adhesive strength (about 0.5 N/cm$^2$) of the conventional hydrogel composition, and accordingly, the sheet type of mask gel composition or the mask sheet including the same may be easily attached to the skin and have excellent delivery effects of active ingredients to the skin.

The adhesive strength of the sheet type of mask gel composition or the mask sheet including the same may be measured by using a texture analyzer.

Figure 3:
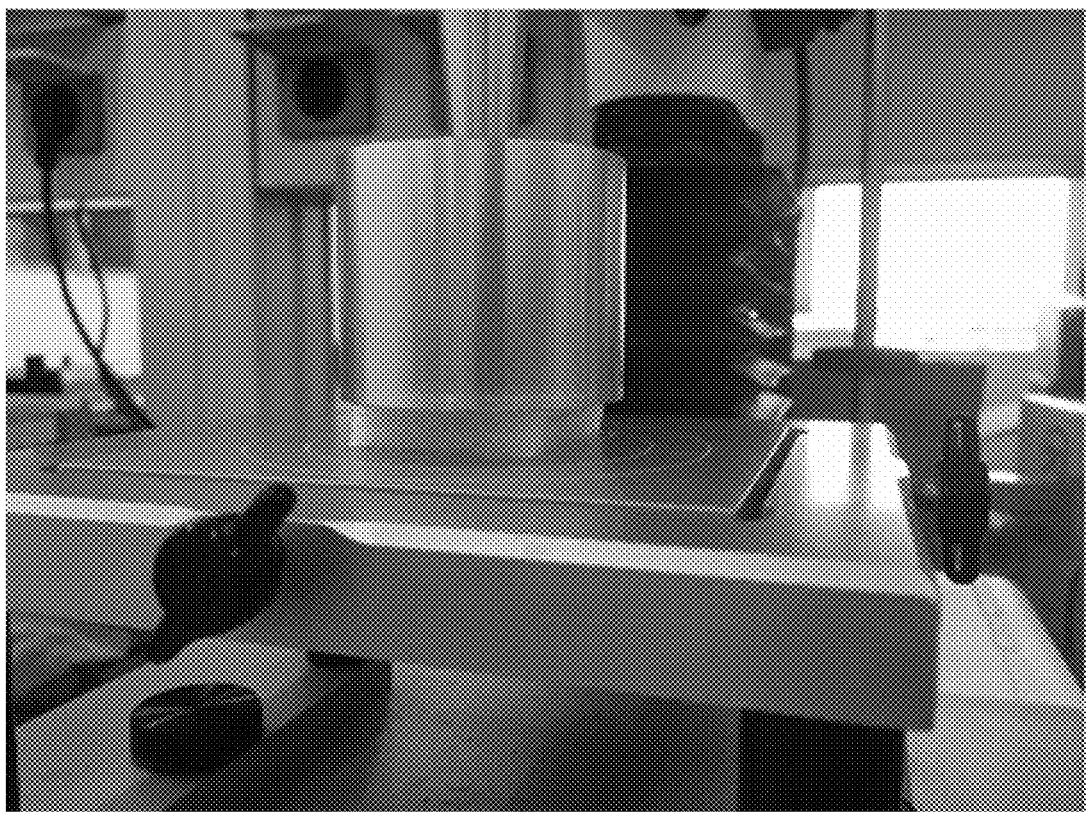

Specifically, as shown in FIG. 3, the gel is fixed with a double-sided adhesive tape after adhering a compression sponge to a plate.

The gel specimen is pressed by about 0.1 mm by lowering a circular jig having a diameter of about 5 cm, and then allowed to stand for about 3 minutes.

After the about 3 minutes, the jig is raised at about 0.2 mm/s to measure maximum strength of separating the specimen and thus obtain adhesive strength of the sheet type of mask gel composition or the mask sheet including the same.

Subsequently, after evenly applying about 0.03 g of a cream (Innisfree Hanran cream) on the surface of the gel, the sample is pressed by about 0.1 mm by lowering the jig, and then allowed to stand for about 3 minutes.

After the about 3 minutes, the jig is raised at about 0.2 mm/s to measure maximum strength and thus obtain adhesive strength of the sheet type of mask gel composition or the mask sheet including the same, when the layering skin care is applied.

The polyol imparts moisturizing and softness to the skin by a plurality of hydroxy groups, and may include any polyhydric alcohol compound without a particular limit. For example, the polyol may include glycerine, 1,3-butanediol, propylene glycol, polyethylene glycol, dipropylene glycol, propanediol, or a combination thereof, but is not limited thereto.

The polyol may be included in an excessive amount, for example about 60 wt % to about 98 wt %, about 70 wt % to about 95 wt %, or about 71 wt % to about 93 wt %, based on a total amount of the sheet type of mask gel composition.

When the polyol is included within the ranges, a refreshing feeling of use as well as the moisturizing and softness may be simultaneously secured.

For example, when the polyol is included in an amount of less than about 60 wt % based on a total amount of the sheet type of mask gel composition, the moisturizing and softness may be deteriorated, and when the polyol is included in an amount of greater than about 98 wt %, the moisturizing and softness may be improved, but stickiness or stuffiness may also be generated.

The water-soluble thickener is not particularly limited, but may be any generally well-known water-soluble thickener.

For example, the water-soluble thickener may include at least one carboxyl group.

The water-soluble thickener may play a role of increasing viscosity of the sheet type of mask gel composition.

The water-soluble thickener may include xanthan gum, hyaluronic acid, carboxymethylcellulose, polyacrylate carboxymethyl starch, carboxymethyl chitosan, carboxymethyl dextran, or a combination thereof, but is not necessarily limited thereto.

The water-soluble thickener may be included in an amount of about 0.01 wt % to about 20 wt %, for example about 1 wt % to about 15 wt %, or about 2 wt % to about 10 wt %, based on a total amount of the sheet type of mask gel composition.

When the water-soluble thickener is included within the ranges, there may be an excellent effect of enhancing viscosity of the gel composition, and an excellent feeling of use may also be obtained.

For example, when the water-soluble thickener is included in an amount of less than about 0.01 wt % based on a total amount of the sheet type of mask gel composition, there may be an insignificant effect of enhancing the viscosity of the gel composition, and when the water-soluble thickener is included in an amount of greater than about 20 wt %, the viscosity of the gel composition may be excessively increased, deteriorating the feeling of use.

The sheet type of mask gel composition and the mask sheet including the same according to an embodiment include very little moisture.

The reason is that water is included in a small amount of less than about 10 wt %, for example, less than about 5 wt %, based on the total weight of the gel composition, and in addition, moisture is even removed through a reaction of the other components of the polyol and the water-soluble thickener.

In this way, since the gel composition is prepared by using the small amount of water, the gel composition and the mask sheet including the same according to an embodiment may not only efficiently deliver oil-soluble active ingredients but also efficiently deliver water-soluble active ingredients by using the water-soluble thickener.

In addition, the gel composition and the mask sheet including the same according to an embodiment have almost no moisture and thus are strong against microbial contaminations, and may also be easily attached to the skin due to higher adhesion than those of a hydrogel and the like and have an excellent delivery effect of active ingredients to the skin.

On the other hand, the sheet type of mask gel composition may further include a wrinkle-improving material such as oleanolic acid, a whitening material, a skin trouble-improving material, or a combination thereof, if necessary.

The oleanolic acid is a functional material having an effect of improving wrinkles, and when the gel composition according to an embodiment further includes the oleanolic acid, the effect of improving wrinkles may be obtained in a shorter time than when other wrinkle-improving functional cosmetics are used.

For example, the sheet type of mask gel composition according to an embodiment includes the functional material having an effect of improving wrinkles such as the oleanolic acid and thus may have a very excellent wrinkle-improving function.

Accordingly, the sheet type of mask gel composition and the mask sheet including the same according to an embodiment may be used for a face but also for a neck. For example, the sheet type of mask gel composition may be a gel composition for a neck band or a gel composition for a neck mask.

(The mask sheet may be a neck band or a neck mask.) Since a neck has more wrinkles than a face, a mask sheet is more difficult to attach on the neck than on the face, and the sheet type of mask gel composition and the mask sheet including the same according to an embodiment have very excellent adhesive strength as aforementioned and thus are well attached to the neck other than the face, and furthermore, when the sheet type of mask gel composition and the mask sheet including the same according to an embodiment include active ingredients for improving wrinkles (e.g., oleanolic acid, etc.), an effect of improving the neck wrinkles is quickly obtained, and accordingly, the sheet type of mask gel composition and the mask sheet including the same may be very suitable for a neck band or a neck mask.

Examples of the wrinkle-improving material may include retinol, retinyl palmitate, polyethoxylated retinamide, adenosine, enzyme-treated red *ginseng* saponin, and the like in addition to the oleanolic acid, and the wrinkle-improving material may be included in an amount of about 0.001 wt % to about 5.0 wt % based on a total amount of the composition, and a type and a content of the wrinkle-improving material are not limited thereto.

Examples of the whitening material may include a mulberry extract, arbutin, an oil-soluble licorice extract, niacineamide, alpha bisabolol, ethyl ascorbyl ether, ascorbyl glucoside, ascorbyl tetraisopalmitate, melasolve, tranexamic acid, and the like, which may be included in an amount of about 0.001 wt % to about 5.0 wt % based on a total amount of the composition, and a type and a content of the whitening material are not limited thereto.

The skin trouble-improving material may include madecassoside, centella asiatice, beta-sitosterol, allantoin, panthenol, tramexamic acid, urea, AHAs, BHAs, potassium licorice, tea tree oil, sulfur, volcanic pine powder, and the like, which may be included in an amount of about 0.001 wt % to about 20 wt % based on a total amount of the composition, and a type and a content of the skin trouble-improving material are not limited thereto.

In addition, the sheet type of mask gel composition may further include ester-based oils, absorption enhancers, or combinations thereof depending on a purpose.

On the other hand, when the sheet type of mask gel composition further includes an oil, a degree of application of the gel composition, such as softness, moisture, adhesion, and the like, may be easily adjusted.

The oil may include mango butter, cocoa butter, almond oil, avocado oil, bees wax, brazil nut oil, caster oil, jojoba oil, mineral oil, olive oil, tocopherol, shea butter, MCT oil (medium chain triglyceride oil) containing about 6 to about 12 carbons, or a combination thereof, but is not necessarily limited thereto.

For example, specific examples of the MCT oil may include caproic acid having about 6 carbons, caprylic acid having about 8 carbons, capric acid having about 10 carbons, lauric acid having about 12 carbons, or a combination thereof, but is not necessarily limited thereto.

The oil may be included in an amount of about 0.5 wt % to about 20 wt %, for example about 3 wt % to about 15 wt %, or about 5 wt % to about 10 wt %, based on a total amount of the sheet type of mask gel composition.

When the oil is included in an amount of less than about 1 wt % based on a total amount of the sheet type of mask gel composition, the gel composition may exhibit a dry feeling of use and unsmooth application, and when the oil is included in an amount of greater than about 20 wt % based on a total amount of the sheet type of mask gel composition, adherence of the gel composition is decreased, deteriorating adhesive strength thereof to the skin.

When the sheet type of mask gel composition further includes a surfactant, the feeling of use of the gel composition may be improved.

The surfactant may include a polysorbate-based compounds, sorbitan stearate, sorbitan oleate, sorbitan sesquioleate, sorbitan isostearate, lecithin, glyceryl laurate, PEG-20, PEG-30, glycol distearate, cetryl glycoside, PG/PG-18/18 dimethicone (cyclopentasiloxane (and) PEG/PPG-18/18 dimethicone), glycol stearate, glyceryl oleate, propyleneglycol monostearate, glyceryl stearate, PEG-30 dipolyhydroxy stearate, PEG-10 dimethicone, cyclopentasiloxane/PEG.PPG-19.19 dimethicone, lauryl PEG.PPG-18.18 m ethicone, cetyl PEG.PP G-10.1 dimethicone, lauryl PEG-9 polydimethylsiloxyethyl dimethicone, a VP/hexadecene copolymer, polyglyceryl-3 polydimethylsiloxyethyl dimethicone, a bis-isobutyl PEG/PP 10/7/dimethicone copolymer, an acrylate/ethylhexyl acrylate/dimethicone metaacrylate copolymer, polyhydroxy stearic acid, polyglyceryl-2 triisostearate, isostearic acid, polyglyceryl-3 polyricinoleate, ethylhexyl palmitate, isopropyl palmitate, or a combination thereof, but is not necessarily limited thereto.

The surfactant may be included in an amount of about 0.1 wt % to about 5 wt %, for example about 0.5 wt % to about 3 wt %, or about 1 wt % to about 2 wt %, based on a total amount of the sheet type of mask gel composition.

When the surfactant is included in an amount of less than about 0.1 wt % based on a total amount of the gel composition, the feeling of use may be deteriorated by the gel composition, and when the surfactant is included in an amount of greater than about 5 wt %, the surfactant may cause an irritation problem.

In addition, the sheet type of mask gel composition according to an embodiment may further include a skin conditioner.

The skin conditioner is a component supplying nutrients to the skin, for example, panthenol, vitamins, niacinamide, adenosine, retinol, melasolve, and an extract such as from aloe, green tea, *ginseng*, pine needles, mulberry leaves, lavender, etc., whose content is not particularly limited.

In addition, the sheet type of mask gel composition according to an embodiment may further include, if necessary, at least one additive (an additive additionally added to a conventional cosmetic composition) such as a preservative, a fragrance, and the like, which will not be illustrated in detail.

The sheet type of mask gel composition may be a composition for wrinkle care, for example, a composition for care for neck wrinkles or a composition for care of wrinkles around the eyes or nasolabial area, and accordingly, a gel composition for a neck mask (neck band), a gel composition for an eye mask, or a gel composition for a facial mask.

Another embodiment includes a mask sheet including the sheet type of mask gel composition.

As aforementioned, the mask sheet may be a neck band, a neck mask, an eye mask, or a face mask, but is not limited thereto.

The mask sheet may be manufactured by a method of manufacturing a mask sheet, which will be described later.

The mask sheet has no particular limit in a shape or a thickness, but may adopt those of a commonly-used mask sheet and the like.

In addition, on the skin-contacting surface of the mask sheet and the like, additional substances such as capsules where cream, oil, and the like are supported may be disposed, and accordingly, within a range of expressing the effects of the sheet type of mask gel composition, any component, substrate, or the like which may enhance skin health may be included in the sheet type of mask gel composition.

The mask sheet may have a support attached to one surface of the mask sheet. The support may be for reducing damage such as folding or tearing of the mask sheet but protecting the skin contact surface of the mask sheet.

The support may be a non-woven fabric or a woven fabric formed of a regenerated fiber such as cotton, rayon, and the like, or a fiber of polyurethane having elasticity, acetate, wool, an ester-based material including polyethylene glycol terephthalate and the like, polyethylene (PE), nylon, polypropylene (PP), or a combination thereof, a support in which oriented polypropylene (OPP), casting polypropylene (CPP), high density polyethylene (HDPE), low density polyethylene (LDPE), linear low density polyethylene (LL-DPE), or the aforementioned material is laminated as a film on the non-woven fabric and the like, but is not limited thereto.

In addition, the support may be transparent in order to impart aesthetics and secure product transparency.

The mask sheet may have a release film attached to the other surface of the mask sheet to which the support is attached.

The release film may be any release film or laminated product thereof which is commonly used in transdermal formulations such as mask pacts, etc., and for example, films formed of polypropylene, polyethylene, polyester, polyvinyl chloride, polyvinylidene chloride, and the like, or papers laminated with the aforementioned materials, but are not limited thereto.

Still another embodiment provides a method of manufacturing the above mask sheet.

The method of manufacturing the mask sheet may include: (a) uniformly applying a stirred mixture of a polyol, a water-soluble thickener, and water to a release film; and (b) performing gelation by heating and cooling after applying the stirred mixture and covering (adhering) a support on the other surface of the stirred mixture where the release film is not attached (the opposite side to which the release film is attached).

A mask sheet manufactured in the manufacturing method may maintain adhesive strength for a long time after being attached to skin, for example, greater than or equal to about 30 minutes, greater than or equal to about 1 hour, greater than or equal to about 2 hours, greater than or equal to about 3 hours, greater than or equal to about 4 hours, greater than or equal to about 5 hours, greater than or equal to about 6 hours, greater than or equal to about 7 hours, greater than or equal to about 8 hours, greater than or equal to about 9 hours, greater than or equal to about 10 hours, greater than or equal to about 11 hours, greater than or equal to about 12 hours, or about 12 hours to about 24 hours.

The method of manufacturing the mask sheet may further include aging the gel attached to the support in order to adjust properties.

In the (b) step, the heating may be performed at about 70° C. to about 120° C. for about 2 minutes to about 30 minutes.

In addition, in the (a) step of stirring the polyol, the water-soluble thickener, and water, an additive such as a wrinkle-improving material, a whitening material, a skin trouble-improving material, a combination thereof, or the like may be further included.

Hereinafter, the present disclosure is illustrated in more detail with reference to examples.

However, these examples are exemplary, and the present disclosure is not limited thereto.

Preparation Example

Compositions according to Preparation Examples 1 to 5 and Comparative Preparation Example 1 were respectively prepared to have each composition shown in Table 1.

After adding a water-soluble thickener and purified water to a polyol, gelation was performed by stirring the mixture at 7000 rpm for 3 minutes with a HOMOMIXER™ (T. K. Homomixer Mark II, PREMIX Corp.).

TABLE 1

(unit: wt %)

| | Preparation Example 1 | Preparation Example 2 | Preparation Example 3 | Preparation Example 4 | Preparation Example 5 | Comparative Preparation Example 1 |
|---|---|---|---|---|---|---|
| purified water | 5 | 5 | 5 | 5 | 5 | 87.4 |
| glycerine | 92.5 | 85 | 85 | 82.5 | 87.45 | 10 |
| 1,3-butanediol | — | — | — | 10 | — | — |
| xanthan gum | 2.5 | 10 | — | 2.5 | 2.5 | 1 |
| hyaluronic acid | — | — | 10 | — | — | — |
| HYGEL ® 20D | — | — | — | — | — | 1.6 |
| ethanol | | | | | 5 | |
| oleanolic acid | — | — | — | — | 0.05 | — |

In Table 1, HYGEL® 20D is a commercially available raw material manufactured by mixing gelling polymers such as carrageenan, locust bean gum, and the like, and specifically, includes 50 wt % of the carrageenan, 20 wt % of the locust bean gum, 10 wt % of agar, 10 wt % of guar gum, 5 wt % of glucose, and 5 wt % of potassium chloride.

EXAMPLES

Example 1

The composition with viscosity (liquid) according to Preparation Example 1 was uniformly coated on a releasing film and then heated and cooled down, and a support was applied on the other surface where the release film was not attached, manufacturing a mask sheet.

Evaluation 1: Loss on Drying Test

The sheet masks according to Preparation Examples 1 to 5 and Comparative Preparation Example 1 were respectively processed to have a thickness of 1 mm and cut into a size of 5 cm×5 cm, and then stored in a drying oven at 45° C. for 60 minutes.

From the weights of the processed gels before putting in the drying oven, lost weights after being stored for 10 minutes, lost weights after being stored for 20 minutes, lost weights after being stored for 30 minutes, lost weights after being stored for 40 minutes, lost weights after being stored for 50 minutes, and lost weights after being stored for 60 minutes were respectively measured, and the results are shown in Table 2 and FIG. 1.

In addition, values according to Equation 1 were calculated and are shown in Table 2.

TABLE 2

(unit: g)

| | Reduced (evaporated) weight | | | | | | | |
|---|---|---|---|---|---|---|---|---|
| | Just before storage | Immediately after 10 minutes of storage | Immediately after storage 20 minutes | Immediately after 30 minutes of storage | Immediately after 40 minutes of storage | Immediately after 50 minutes of storage | Immediately after 60 minutes of storage | Value according to Equation 1 |
| Preparation Example 1 | 0 | 1.4 | 2.1 | 2.7 | 3.1 | 3.6 | 3.7 | 3.7 |
| Preparation Example 2 | 0 | 1.5 | 2.3 | 2.8 | 3.2 | 4.0 | 4.0 | 4.0 |
| Preparation Example 3 | 0 | 1.5 | 2.3 | 2.9 | 3.2 | 4.0 | 4.1 | 4.1 |
| Preparation Example 4 | 0 | 1.4 | 2.1 | 2.7 | 3.1 | 3.5 | 3.6 | 3.6 |
| Preparation Example 5 | 0 | 1.4 | 2.3 | 3.0 | 3.3 | 3.9 | 4.3 | 4.3 |
| Comparative Preparation Example 1 | 0 | 13.7 | 26.4 | 41.5 | 53.1 | 62.4 | 71.0 | 71.0 |

Referring to Table 2, the gel composition according to an embodiment and a mask sheet including the same exhibited no weight change after 60 minutes, but the hydrogel composition of Comparative Preparation Example 1 exhibited 71% weight loss from the initial weight after 60 minutes.

Accordingly, the gel composition according to an embodiment and the mask sheet including the same maintained the initial adhesive strength.

Evaluation 2: Adhesive Strength when Layering Skin Care is Applied

After evenly applying 0.03 g of a cream (Innisfree Hanran Cream) onto the gel composition according to Preparation Example 1, the gel composition applied with the cream was pressed down by 0.1 mm by lowering a jig, and then allowed to stand for 3 minutes.

After 3 minutes, the jig was lifted at 0.2 mm/s to measure maximum strength, adhesive strength of the sheet type of mask gel composition or a mask sheet including the same was measured, when a layering skin care was applied, and as a comparative example, adhesive strength of an SRP smoothing neck patch made by an M company was measured in the same method.

The experiment was repeated three times with respect to each one and averaged, and the results are shown in Table 3.

TABLE 3

| No. | Preparation Example 1 is used alone | Use of Preparation Example 1 after applying the cream | M company product is used alone | Use of M company product after applying the cream |
|---|---|---|---|---|
| 1 | 0.72 | 1.23 | 0.35 | 0.33 |
| 2 | 0.67 | 1.09 | 0.49 | 0.33 |
| 3 | 0.64 | 1.10 | 0.55 | 0.46 |
| average | 0.68 | 1.14 | 0.46 | 0.38 |
| deviation | 0.04 | 0.08 | 0.10 | 0.08 | unit: N/cm²

Referring to Table 3, the gel composition according to Preparation Example 1 exhibited excellent adhesive strength, when used alone and when subsequently used after using the cream, compared with the product of the M company.

Above all, the gel composition of Preparation Example 1 exhibited higher adhesive strength, when subsequently used after using the cream than when used alone, but the product of the M company exhibited higher adhesive strength when used alone than when subsequently used after using the cream.

Evaluation 3: Neck Wrinkle Improvement Performance

A clinical experiment was performed by dividing Group A (20 people) using the mask sheet according to Example 1 alone on an area with neck wrinkles and Group B (20 people) subsequently using the mask sheet according to Example 1 on the area with neck wrinkles after applying an essence containing a wrinkle-improving ingredient on the area with neck wrinkles and equally making them use the product overnight once a day for 4 weeks.

Each improvement degree of neck wrinkles was examined right before the clinical experiment, after 2 weeks, and after 4 weeks by using a PRIIVIOS™ Lite instrument, and the results are shown in Table 4.

A specific measurement method by using the PRIIVIOS™ Lite instrument is as follows.

Each improvement degree of neck wrinkles after using a cream and a toner for 2 weeks and 4 weeks was measured by using the PRIMOS™ Lite instrument (field of view 18 times flexible 3D measuring, GFMesstechnik GmbH) according to the instrument manual.

Using the PRIIVIOS™ Lite instrument, the same testing person fixed a testee's face to a specially-made PRIMOS™ face fixation device set, and then adjusted a measurement area, the tip of eyes, into a focus pattern of the PRIIVIOS™ Lite instrument for measurement reproducibility of a neck area, and the neck area was measured.

TABLE 4

| | Group A | Group B |
|---|---|---|
| Clinical progress (0 week) | 41.32 | 33.60 |
| 2 weeks | 38.26 | 29.04 |
| 4 weeks | 36.58 | 27.04 |

(unit: μm)

Referring to Table 4, Group B exhibited significantly reduced neck wrinkles of 13.57% after 2 weeks and 19.52% after 4 weeks, and Group A exhibited significantly reduced neck wrinkles of 11.47% after 4 weeks.

Considering that in general, clinical trials of cosmetics aimed at improving wrinkles evaluate an improvement degree of the wrinkles after applying the cosmetics around eyes for 8 weeks or more, and even if there are differences depending on a type and formulation of active ingredients, the effect of improving wrinkles is approximately 6% to 8%, both Group A and Group B exhibited excellent neck anti-wrinkle effects.

Furthermore, when the mask sheet according to the embodiment was attached after first applying an essence containing a wrinkle-improving component to a neck wrinkle area, synergy occurred, obtaining a high wrinkle-improving effect of 13.57% with only 2 weeks' use.

This aforementioned wrinkle-improving effect in the neck area, where the wrinkle improving effect was relatively more difficult to obtain than in the eye area, was a remarkable clinical effect, compared with that of conventional wrinkle improvement cosmetics, and accordingly, the mask sheet according to an embodiment had very excellent functionality as a neck band or a neck mask.

While this invention has been described in connection with what is presently considered to be practical example embodiments, it is to be understood that the invention is not limited to the disclosed embodiments. On the contrary, it is intended to cover various modifications and equivalent arrangements included within the spirit and scope of the appended claims.

What is claimed is:

1. A sheet mask gel composition, comprising a polyol, a water-soluble thickener, and water,
    wherein the water is included in an amount of less than about 10 wt % based on a total weight of the sheet mask gel composition,
    wherein the sheet mask gel composition, when applied to skin of a mammal, maintains at least about 80% of an initial adhesive strength expressed in unit of N/cm² for greater than or equal to about 30 minutes,
    wherein the sheet mask gel composition satisfies Equation 1:

$$100-(B/A \times 100) < 10 \qquad \text{Equation 1}$$

wherein A is a weight immediately after the gel composition is prepared and cut to a size of 5 cm×5 cm×1 mm, and B is a weight immediately after drying the gel composition at 45° C. for 60 minutes; and
    wherein the polyol is included in an amount of about 60 wt. % to about 98 wt. % based on a total amount of the sheet mask gel composition.

2. The sheet mask gel composition of claim 1, wherein the sheet mask gel composition has higher adhesive strength when the sheet mask gel composition is applied to the skin of a mammal, after applying a water-soluble or oil-soluble composition to the skin of a mammal than when the sheet mask gel composition alone is applied directly to the skin of a mammal.

3. The sheet mask gel composition of claim 1, wherein the sheet mask gel composition further comprises a wrinkle-improving material, a whitening material, a skin trouble-improving material, or a combination thereof.

4. The sheet mask gel composition of claim 1, wherein the sheet mask gel composition has adhesive strength of greater than or equal to about 0.6 N/cm².

5. The sheet mask gel composition of claim 1, wherein the polyol comprises glycerine, 1,3-butanediol, propylene glycol, polyethylene glycol, dipropylene glycol, propanediol, or a combination thereof.

6. The sheet mask gel composition of claim 1, wherein the water-soluble thickener is included in an amount of about 0.01 wt % to about 20 wt % based on a total amount of the sheet mask gel composition.

7. The sheet mask gel composition of claim 1, wherein the water-soluble thickener comprises a xanthan gum, hyaluronic acid, carboxymethyl cellulose, polyacrylate carboxymethyl starch, carboxymethyl chitosan, carboxymethyl dextran, or a combination thereof.

8. The sheet mask gel composition of claim 1, wherein the sheet mask gel composition is a gel composition for a neck band, a gel composition for a neck mask, a gel composition for an eye mask, or a gel composition for a facial mask.

9. A mask sheet comprising the sheet type mask gel composition of claim 1.

10. The mask sheet of claim 9, wherein the mask sheet is a neck band, a neck mask, an eye mask, or a facial mask.

11. The mask sheet of claim 9, wherein the mask sheet has a support attached to one surface of the mask sheet.

12. The mask sheet of claim 11, wherein the support is a regenerated fiber; a polyurethane; an ester-based material; a nonwoven fabric or a woven fabric made of a fiber of polyethylene, nylon, polypropylene, or a combination thereof; oriented polypropylene; casting polypropylene; high density polyethylene; low density polyethylene; linear low density polyethylene; or a support in which the ester-based material is laminated to the nonwoven fabric in the form of a film.

13. The mask sheet of claim 11, wherein the mask sheet has a release film attached to the other surface of the mask sheet to which the support is attached.

14. The mask sheet of claim 13, wherein the release film is:
    (a) polypropylene, polyethylene, polyester, polyvinyl chloride, or polyvinylidene chloride; or
    (b) paper on which (a) is laminated.

15. A method of manufacturing the mask sheet of claim 9, comprising:
    (a) uniformly applying a stirred mixture of a polyol, a water-soluble thickener, and water to a release film;
    (b) heating and cooling (a) to perform gelation; and
    (c) attaching a support to the surface on which the release film is not applied to manufacture the mask sheet,
    wherein the mask sheet maintains at least about 80% of the initial adhesive strength after being adhered to the skin of a mammal for about 30 minutes.

16. The method of claim 15, wherein the method further comprises aging the gel attached to the support.

17. The method of claim 15, wherein the heating is performed at a temperature of about 70° C. to about 120° C. for about 2 minutes to about 30 minutes.

18. The method of claim 15, wherein the stirred mixture of the polyol, the water-soluble thickener, and water further comprises a wrinkle-improving material, a whitening material, a skin trouble-improving material, or a combination thereof.

* * * * *